United States Patent [19]

Williams

[11] Patent Number: 5,277,195
[45] Date of Patent: Jan. 11, 1994

[54] PORTABLE SPIROMETER

[75] Inventor: David R. Williams, San Diego, Calif.

[73] Assignee: Dura Pharmaceuticals, Inc., San Diego, Calif.

[21] Appl. No.: 829,717

[22] Filed: Feb. 3, 1992

[51] Int. Cl.$^5$ .............................................. H61B 5/08
[52] U.S. Cl. .................................. 128/725; 128/720; 128/726; 73/861.75; 73/861.76; 482/13
[58] Field of Search ........................ 128/720, 725, 726; 73/861.75, 861.76; 482/13

[56] References Cited

U.S. PATENT DOCUMENTS

| | | | |
|---|---|---|---|
| 2,724,969 | 11/1955 | Bloser | 73/861.75 |
| 4,073,189 | 2/1978 | Draper | 73/861.75 |
| 4,294,262 | 10/1981 | Williams et al. | 128/726 |
| 4,991,591 | 2/1991 | Jones et al. | 128/725 |

FOREIGN PATENT DOCUMENTS 2236395  4/1991  United Kingdom ................ 128/725

OTHER PUBLICATIONS

Mostardi et al. (1979), Microprocessor Application to Standard Spirometry, *Journal of Clinical Engineering*, vol. 4 No. 4, Oct.-Dec., pp. 347-351.

"Wright Peak Flow Meter" Brochure (1989) and photographs.
"Wright Pocket Peak Flow Meter" Brochure (undated) and photographs.

*Primary Examiner*—Lee S. Cohen
*Assistant Examiner*—Brian L. Casler
*Attorney, Agent, or Firm*—Lyon & Lyon

[57] ABSTRACT

A portable hand-held spirometer capable of being accommodated in a pocket or handbag, comprising a chassis, an enclosed curved passageway in communication with the chassis including an inlet, for receiving the forced expiration of the user, and an outlet, through which the expiration may be exhausted, a vane pivotally mounted in the passageway, between the inlet and the outlet, for moving under the influence of the user's forced expiration from a first position closing off the passageway to a succession of other open positions forming an ever widening gap between the vane and part of the passageway as the vane moves therethrough, a bottom cover for incrementally measuring various positions of the vane, throughout its travel as a function of time, a device to convert the measurements to various diagnostic parameters applicable to the user's lung condition, and a device to report the values.

32 Claims, 3 Drawing Sheets

PORTABLE SPIROMETER

BACKGROUND OF THE INVENTION

1. Field of the Invention

This invention pertains to human ventilatory measurement instruments. More particularly, it concerns a portable hand-held spirometer for measuring pulmonary function and reporting the results as a plurality of lung function parameters.

2. Description of the Prior Art

A spirometer is a form of spiro analyzer or ventilometer and is generally defined as an instrument for measuring the breathing capacity and other bronchial activity of the lungs. Spirometers find wide utilization in the diagnosis of lung and breathing difficulties such as emphysema, asthma and chronic bronchitis. More particularly, they have found use in monitoring the progress of recipients of lung transplants. Ordinarily, spirometers involve large equipment located in laboratories or doctors' offices. The testing requires the patient to breath into the equipment with a forced expiration.

The parameters obtained through the use of spirometers are reported in well-accepted formats such as "forced vital capacity" (FVC) which is the volume of air that is exhaled following a maximum single breath regardless of the time taken; "peak expiratory flow" (PEF) which is a measure of the highest flow rate of air from the lungs during a single forced expiration; "forced expired volume during the first second" ($FEV_1$) which represents the volume of air that can be exhaled forcibly in one second; "$FEF_{25/75}$" which is the average expiratory flow for the middle 50% of the expiration; and, other combinations of these values such as $FEV_1$ expressed as a percentage of the FVC. Depending upon the particular malady involving the lungs, the physician or physiotherapist may choose to look at one, some, all of these parameters, or other ones.

Large electronic spirometers situated in a laboratory or doctor's office are often massive and quite expensive and therefore not installed at many locations, thereby requiring the patient to travel substantial distances to undergo the testing. There are some small, hand-held, portable meters presently available, however, they measure only peak flow. There are also some portable electronic spirometers available, however, they measure only a few parameters of lung function and their cost is such that few, if any, individuals can afford them for home monitoring. Further, because of the lack of multiple parameter reporting, the treating physician is often left with only partial results which deprive him or her of a more complete analysis of the patient's lung condition.

Some of these units require the patient to record the results of the tests and bring them to the physician's office for later analysis. This practice can result in errors in recording and evaluating the data. Accordingly, there exists in the spirometer field, a significant and continuing need for a portable spirometer that measures many or all of the desired parameters, priced to be economically affordable by most patients, and that would automatically record the results for reporting to the user or to the physician's office for analysis.

SUMMARY OF THE INVENTION

This invention is a portable spirometer that satisfies all of the needs heretofore existing in the prior art. It is of small physical size so that it may be accommodated in a pocket or handbag and easily used by both left-handed and right-handed persons. Very importantly, it measures multiple parameters of pulmonary functions and displays the parameters and stores the data in a compact memory thus eliminating the errors frequently associated with manually logged results. The spirometer accurately measures the following functions: FVC, PEF, $FEV_1$, $FEF_{25/75}$, $FEV_1/FVC$, and records them in a memory that may later be interconnected with a base unit with built-in printer and charger or through a modem for instantaneous transfer directly to the doctor's office for immediate analysis.

This novel device contains a selector switch that may be preset to measure and record only certain parameters or the unit's full range of parameters thereby providing the physician with an extremely versatile tool. The unit is modest in price and ergonomically designed to encourage easy and reassuring use by the patient in the privacy of their home. It has a tactile operations button for easy use by the owner and uses a sterilizable plastic or a disposable cardboard breathing tube for cleanliness. The device includes a removable cover for gaining access to the interior passageway to clean it, remove moisture and undertake other house cleaning chores.

A liquid crystal display is built into the unit for easy readout of the results of the test, as well as such caretaker's functions as to call attention to a low battery or to have the user repeat the procedure should something have occurred during the initial forced expiration to require re-testing. The unit of this invention is eminently suitable for all aspects of respiratory measurement and is wholly confined within a small unit easily held in one's hand.

Accordingly, the main object of this invention is a portable, hand-held spirometer capable of use by a patient conveniently in their home, in public or in a physician's office to measure and report with improved accuracy any and all of the lung function parameters pre-set for measurement in the unit. Other objects of the invention include a device capable of being accommodated in a pocket or handbag; a device useable by persons of all age, notwithstanding whether they are left-handed or right-handed; a device that records the five most commonly used tests of lung function and stores them for later recording or electronic transmission to the office of the treating physician or otherwise; a device that records the values of the lung parameters in a tamper-proof memory thereby eliminating errors that frequently are associated with manually logged results; a device that is modest in price and ergonomically designed to encourage easy and reassuring use; a device that may be used by persons of all ages by merely pressing a single tactile button; a device that uses a disposable cardboard or sterilizable plastic tube for cleanliness; and, a device for the personal use by a person in the convenience of one's own surroundings for home monitoring of disease progress, medication titration, and early warning advice for seeking timely professional help. Still other objects include a device that displays the lung function parameters on a liquid crystal display for easy observation; and, a device that is eminently suitable for all respiratory measurement and that is wholly confined within a small body easily handled by a single individual.

These and other objects of the invention will become more apparent when reading the description of the preferred embodiment along with the drawings that are appended hereto. The protection sought by the inventor may be gleaned from a fair reading of the claims that conclude this specification.

DESCRIPTION OF THE PREFERRED EMBODIMENT

Figure 1:
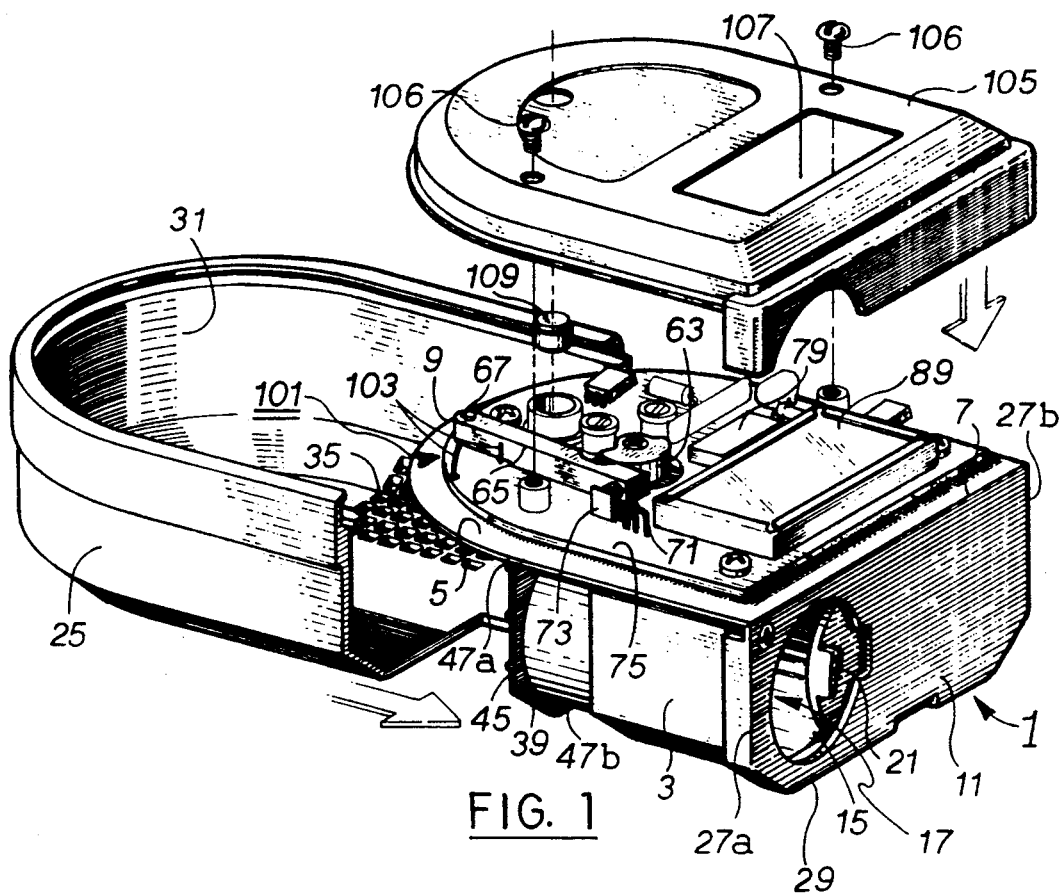
FIG. 1 is a trimetric, exploded view of the chassis and top and bottom covers making up the preferred embodiment of this invention.
Figure 2:
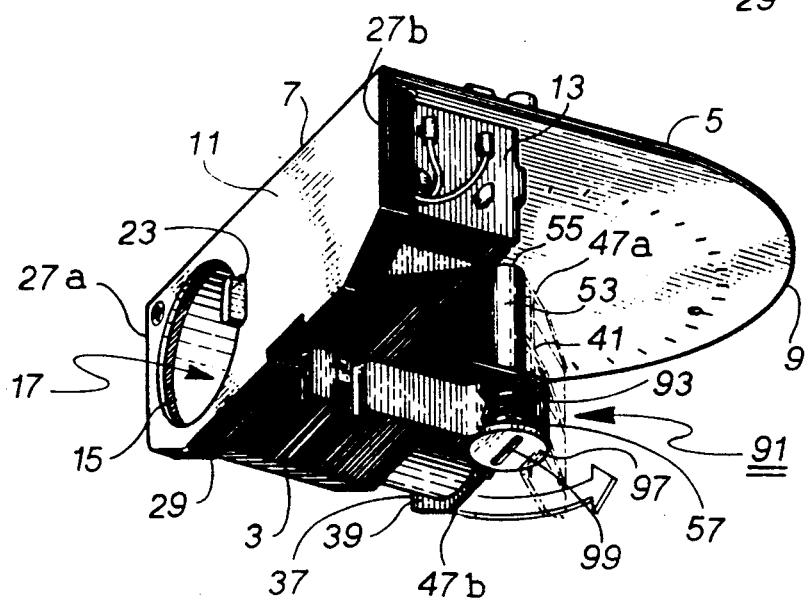
FIG. 2 is a trimetric view, with partial cutaway, of the underside of the chassis of the same embodiment as shown in FIG. 1.
Figure 3:
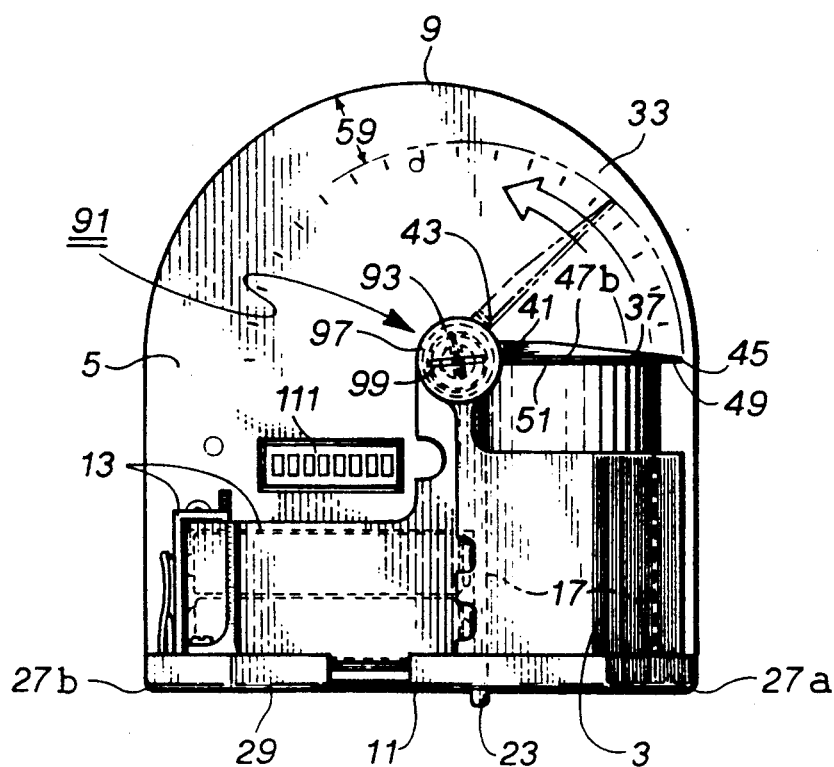
FIG. 3 is a bottom plan view of the chassis showing the travel of the vane through the air passageway.

Turning now to the drawings wherein like elements are identified with like numerals throughout the six figures, FIGS. 1, 2 and 3 show the spirometer 1 of this invention to have a chassis 3 comprising a broad top plate 5 defined by a straight front edge 7 and a U-shaped edge 9 extending rearward from the terminal ends thereof. A front surface 11 depends from front edge 7 a short distance to form the front wall of the spirometer. A closable battery box 13 is nested behind front wall 11 and under top plate 5 which will hereinafter be more fully explained.

An aperture 15 is formed in front wall 11 preferably to one side thereof forming the opening to a bore 17 that extends rearward therefrom and interior said spirometer. A short tube 19 either of disposable cardboard or reusable plastic is provided for insertion in bore 17 to facilitate blowing into the spirometer. A small door 21 is slidably received in front wall 11 and arranged to be moved by a handle or projection 23 back and forth to facilitate covering and uncovering aperture 15 as desired as a guard to keep foreign matter out of the interior of the spirometer when it is not in use.

A bottom cover 25 is provided for attachment about chassis edge 9, the spaced-apart sides 27a and 27b and bottom edge 29 of front wall 11. Cover 25 extends rearward from bottom edge 29 to an upwardly extending U-shaped rear wall 31 then upwardly to join with U-shaped chassis rear edge 9. Bottom cover 25 thus forms along with chassis plate 5 a curved passageway 33, of general rectangular cross-section, interior of the spirometer. A series of apertures 35 are formed in bottom cover 25 and closely spaced together, preferably on the opposite side of cover 25 from where aperture 15 is located in front wall 11 to provide an outlet as will be more fully explained.

A vane 37 is pivotally mounted in passageway 33, preferably on the inside radius of the curvature thereof. Vane 37 is defined by a flat plate 39, reinforced with cross-ribs 41, extending outward from a pivotal edge 43 to an outer edge 45 and joined together through spaced-apart top and bottom edges 47a and 47b, respectively. Vane 37 is arranged to swing from a first position 49 at the inner end 51 of bore 17 and across passageway 33 through a succession of other positions further into curved passageway 33, urged therethrough by the forced expiration of the user's breath into bore 17. Top and bottom vane edges 47a and 47b are arranged to swing in the arch in close proximity with the under surface of top plate 5 and the top surface of bottom cover 25 that formed the top and bottom of passageway 33. The term "close proximity" is meant to indicate a gap therebetween of a few thousandths of an inch. The outer edge 45 of vane 37 is made straight and aligned such that it too moves into close contact, i.e. a few thousandths of an inch, with the inside surface of cover rear wall 31 when vane 37 is in its first position at the inner end 51 of bore 17.

Preferably, curved passageway 33 is of a fixed radius and vane 37 is mounted off-center from the center of curvature thereof by a shaft 53 built into or made a part of vane pivotal edge 43. Van shaft 53 extends upward through an aperture 55 formed in chassis plate 5 and extends downward into a short cylinder 57 formed on chassis 3.

As vane 37 pivots about pivotal edge 43 away from inner bore end 51 or first position 49, there is created an ever-increasing gap 59, shown in dotted line in FIG. 3, between vane outer edge 45 and the inside surface of rear wall 31 thereby allowing more and more forced air to pass through passageway 33 and out exhaust apertures 35. This construction allows spirometer 1 to sense flows of air from a minimum of about 2 liters per minute to a maximum of about 800 liters per minute and therefore covers a far wider range of air flows than is currently possible with existing portable units. This renders spirometer 1 usable by a wide range of individuals whose lung size may vary such as from a small child through large adults to the elderly.

A first means 61 is provided for rapidly and accurately measuring the incremental change of positions of vane 37 as it rotates through its arch in air passage 33 under the positive pressure of the forced expiration of air by the user blown into aperture 15 and out exhaust apertures 35. It is through these rapid incremental measurements over time of the different positions of vane 37, that FVC, PEF, FEV, and other particular lung function parameters are calculated.

Figure 4:
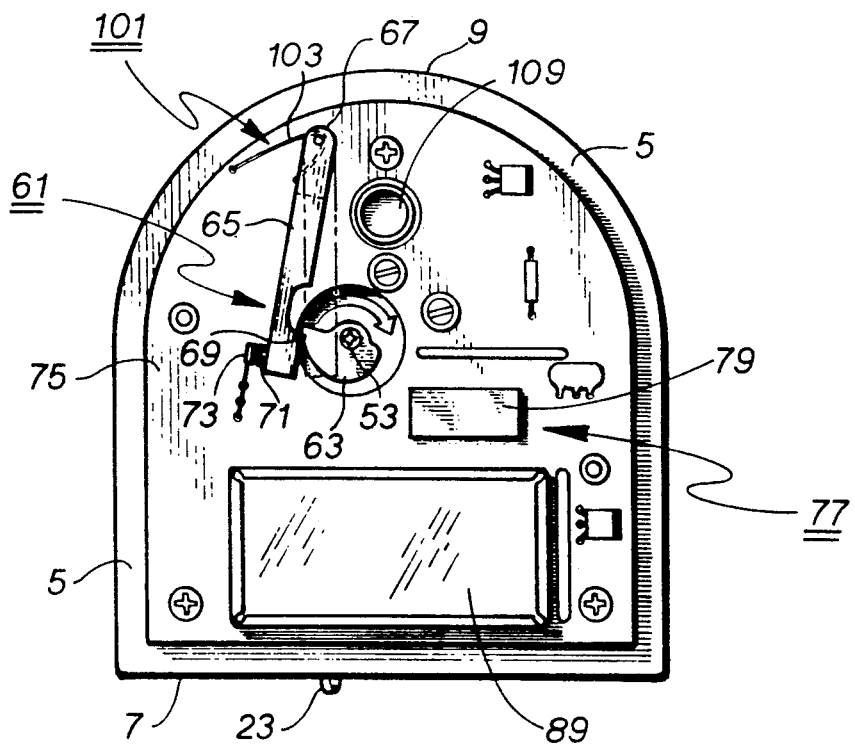
FIG. 4 is a top plan view of the chassis showing the printed circuit board and associated hardware.
Figure 5:
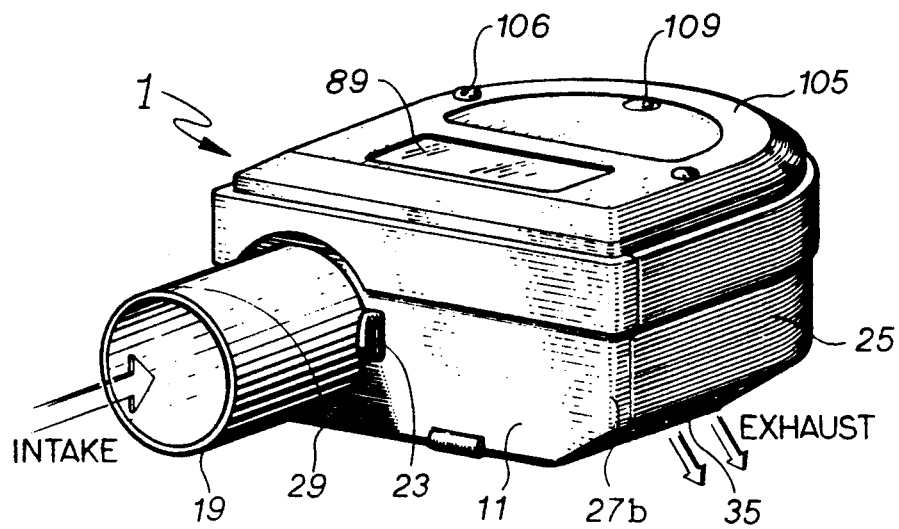
FIG. 5 is a trimetric view of the assembled embodiment showing the blowing tube inserted therein; and, FIG. 6 is a block diagram of the electronic components of the invention.
Figure 6:
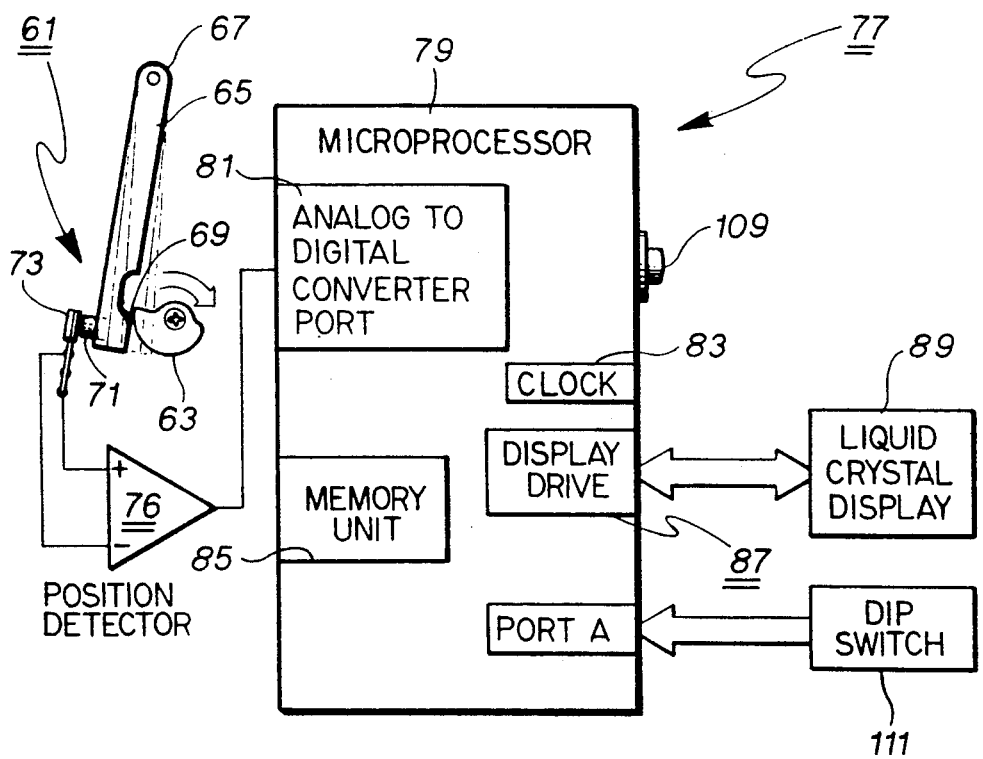

As shown more particularly in FIGS. 1, 4 and 6, first means 61 includes a cam lobe 63 attached to vane shaft 53 and preferably mounted such that the plane of the cam lobe is perpendicular or normal to the axis of pivotal edge 43. Cam lobe 63 is attached to vane pivotal edge 43 by shaft 53 so that it is rotated by the pivotal movement of vane 37. A sensor arm 65 is pivotally mounted at one end 67 and extends toward cam lobe 63. A cam following surface 69 is formed on sensor arm 65 and adapted to contact cam lobe 63 for movement there against.

A small permanent magnet 71 is attached to sensor arm 65. A Hall Effect device 73 is mounted independently of permanent magnet 71, preferably on a circuit board 75 that is mounted atop and parallel to chassis plate 5 and is positioned near magnet 71 so as to measure the magnetic flux variations generated by the movement of magnet 71.

As shown in FIGS. 1, 4 and 6, as vane 37 is rotated by the forced expiration of air traveling through passageway 33, cam lobe 63 is caused to rotate and shifts the position of sensor arm 65 so as to move magnet 71 closer to or further away from Hall Effect device 73. Such movement causes a change in the magnetic lines of flux entering Hall Effect device 73 and generates analog data through a position detector 76 as to the position of vane 37 and any particular point in air passageway 33. A second means 77 is provided to convert the analog data generated by detector 7 through relative movement between Hall Effect device 73 and magnet 71 into digital data for determining the various diagnostic parameters applicable to the user's lung condition as determined by the forced expiration into spirometer 1 to move vane 37.

As shown in FIG. 6, second means 77 includes a microprocessor 79 connected as is already known in the art and including an analog-to-digital converter 81 and a clock 83 to provide a plurality of time segments over which the analog measurements may be made to create the digital information. It is preferred that clock 83 be arranged to provide a multiplicity of time units, such as 150 separate time frames per second, in which vane 37 would be measured as to its position in passageway 33 throughout the forced expiration by the user.

Such information, gathered in light of the ever-widening gap 59 created during the forced expiration by the user, may be readily converted to digital information that can be computed, based upon known parameters already inputted to a memory unit 85 of microprocessor 79 to compute the forced vital capacity (FVC), the forced expired volume during the first second ($FEV_1$), the peak expiratory flow (PEF), $FEV_1$ as a fraction of FVC expressed as a percentage, and $FEV_{25-75}$. A third means, such as a display drive 87, for displaying the data, such as a liquid crystal display 89 is provided and preferably mounted on circuit board 75.

A fourth means 91, shown in FIG. 3, is provided along with vane 37 to render an adjustable bias to vane 37 in either direction. One embodiment of fourth means 91 is shown in FIG. 2 to include a coil spring 93, positioned near vane pivotal edge 43 wherein one end of coil spring 93 is attached to vane shaft 53 and the other end attached to a cap 97 that fits tightly by friction down into cylinder 57. A small slot 99 is formed in cap 97 to receive the blade of a standard screwdriver to twist or reposition cap 97 and spring 93 one way or the other to increase or decrease the bias on vane 37. This is useful in calibrating the spirometer.

A fifth means 101, shown in FIG. 4, is also provided, preferably in the form of a spring 103 bearing against sensor arm 65 near its pivotal mounting 67 to bias sensor arm 65 against cam lobe 63 to effect more accurate movement of permanent magnet 71 through the rotation of cam lobe 63. A top cover 105 is provided for positioning over circuit board 75, fastened thereto with screws 106, and, along with front wall 11 and bottom cover 25, enclosing spirometer 1. A window 107 is formed in top cover 105 over liquid crystal display 89 through which one may observe the readouts as they occur.

A tactile button start and sequence switch 109 is provided to be pressed to start a testing sequence. Various user friendly directions are programmed to appear in display 89 such as "PLEASE BLOW", "READY", "BLOW AGAIN" or a symbol denoting low battery or other such information. The results of the test are preferably programmed to appear on liquid crystal display 89 in a sequence of readings that each remain on the display for approximately five seconds. Advancing the readout of the aforesaid calculations can be accomplished more rapidly by pressing switch 109. Holding the switch down for longer than five seconds will re-set the device for another blow. As the readouts are made to appear in display 89, they are also recorded in memory unit 85 for later viewing or transfer via a modem to the physician's office for analysis.

As shown in FIGS. 3 and 6, a dip switch (dual in-line package switch) 111 is preferably located under bottom cover 25 for use by the physician or other monitoring person to select specific lung parameters that are to be viewed.

Chassis 3, top plate 5, front wall 11, bottom cover 25, top cover 105 and many of the various components therein are most conveniently made from plastics, both for light weight and for ease of manufacturing. Battery box 13 holds one or a plurality of batteries to power the computer and other electronic hardware. Bottom cover 25 is preferably made removable from chassis 3 for ease in changing the batteries, cleaning the air passageways, and selecting various positions in dip switch 111 to isolate certain parameters apart from one another.

The spirometer is prepared for use by using tactile button 109, inserting air tube 19 in bore 17, and blowing in one continuous blow into tube 19. The forced air will move vane 37 from its first position across passageway 33, near the inner end of bore 17, through an arch about its pivot shaft 53 and through a succession of other open positions while forming ever-widening gap 59. The air is exhausted through exhaust apertures 85 while second means 77 measures the changing positions of vane 37. Third means 87 converts the analog data to digital data that is displayed on liquid crystal display 89.

While the invention has been described with reference to a particular embodiment thereof, those skilled in the art will be able to make various modifications to the described embodiment of the invention without departing from the true spirit and scope thereof. It is intended that all combinations of elements and steps which perform substantially the same function in substantially the way to achieve substantially the same result are within the scope of this invention.

What is claimed is:

1. A portable, hand-held spirometer comprising:
   a) a chassis;
   b) an enclosed curved passageway in communication with said chassis including an inlet, and an outlet;
   c) a vane pivotally mounted in said passageway, between said inlet and said outlet, and movable from a first position substantially closing off said passageway to a succession of other positions forming a widening gap between said vane and part of said passageway as said vane moves therethrough;
   d) measuring means for measuring positions of said vane, as a function of time;
   e) converting means for converting measured positions of said vane to diagnostic parameters;
   f) reporting means for reporting the diagnostic parameters; and
   g) biasing means for applying a variable bias to said vane to calibrate the spirometer.

2. The spirometer of claim 1 further including a moveable door slidably positioned in said inlet for closing off said inlet when said spirometer is not in use.

3. The spirometer of claim 1 wherein said enclosed curved passageway has a fixed radius and said vane is pivotally mounted offset from the radius of curvature thereof.

4. The spirometer of claim 1 further including a bore spanning said inlet and said passageway, wherein said passageway has a generally rectangular cross-section and said vane is of a size and shape to fit transversely therein at the intersection of said passageway and said bore.

5. The spirometer of claim 1 wherein said means for applying a variable bias comprises:
a) a cylinder attached to said chassis;
b) a spring in said cylinder for applying a tension to said vane and having a first end and a second end with said first end connected to said vane;
c) a cap positioned in said cylinder and connected to said second end of said spring; and
d) tool receiving means on said cap for receiving a tool to rotate said cap to a new position increasing or decreasing the tension of said spring on said vane.

6. The spirometer of claim 1 further including at least one cover removably attached to the chassis to permit cleaning of the interior thereof.

7. The spirometer of claim 1 further including a battery box retaining at least one battery therein, said battery connected to said measuring means.

8. A portable hand-held spirometer comprising:
a) a chassis;
b) a lower cover attached to the chassis and forming with the chassis an enclosed curved passageway of fixed radius including an inlet and inlet bore, and an outlet;
c) a vane pivotally mounted in said passageway on a shaft and offset from the radius of curvature thereof and movable from a first position at one end of said inlet bore to a succession of other positions removed therefrom while forming an ever widening gap between said vane and part of said passageway as said vane rotates through said passageway;
d) first means for incrementally measuring various positions of said vane, throughout its travel as a function of time;
e) second means to convert said measurements to various diagnostic parameters applicable to the user's lung condition;
f) third means to report said parameters;
g) an upper cover covering said first, second and third means; and
h) a dual in-line package switch linked to the second means for pre-selecting the diagnostic parameters desired to be reported.

9. The spirometer of claim 8 wherein said first means includes:
a) a cam lobe including a cam surface attached to said vane, normal to the axis of said shaft, and arranged to rotate as a function of vane movement;
b) a sensor arm including a cam following surface extending into contact with said cam lobe;
c) a magnet attached to said sensor arm for moving through a path as a function of vane movement; and,
d) a Hall Effect device mounted apart from said magnet for receiving a variable pattern of lines of flux from said magnet as a function of vane position.

10. The spirometer of claim 8 wherein said second means includes:
a) a microprocess including a clock for computing the position of said vane, as a function of time, and producing analog data therefrom; and,
b) an analog-to-digital converter attached to said microprocessor including a memory unit to produce digital diagnostic parameter values from the analog data.

11. The spirometer of claim 8 wherein said third means includes a liquid crystal display, connected to said second means to display diagnostic parameters.

12. The spirometer of claim 8 further including a separate disposable tube inserted in said inlet for use by the user as a blowing tube.

13. The spirometer of claim 8 further including a moveable door slidably positioned in said inlet for closing of said inlet when said spirometer is not in use.

14. The spirometer of claim 8 wherein said outlet comprises a plurality of closely spaced apertures.

15. The spirometer of claim 8 further including battery means to provide electrical power to said first, second and third means.

16. A portable spirometer comprising:
a housing including a curved passageway having an inlet and an outlet;
a vane pivotally mounted in said passageway, between said inlet and said outlet;
a cam attached to and pivotable with said vane;
a sensor arm contacting said cam;
a Hall effect device and a magnet associated with the sensor arm for detecting positions of the arm and correspondingly positions of the vane;
processing means, linked to the Hall effect device, for determining a diagnostic parameter; and
reporting means for reporting the diagnostic parameter.

17. The spirometer of claim 16 wherein said processing means includes:
a) a microprocessor including a clock for computing the position of said vane, as a function of time, and producing analog data therefrom; and,
b) an analog-to-digital converter linked to said microprocessor and including a memory unit to produce digital diagnostic parameter values from the analog data.

18. The spirometer of claim 17 wherein said reporting means includes a liquid crystal display, connected to said analog-to-digital converter to display said digital diagnostic parameter values.

19. The spirometer of claim 17 further comprising means for tension said sensor arm against said cam.

20. The spirometer of claim 19 wherein said means for tensioning includes a spring bearing against said sensor arm to bias it into contact with said cam.

21. The spirometer of claim 16 further comprising a battery box within the housing for holding a battery to power the processing means and the reporting means.

22. The spirometer of claim 16 further comprising means for tensioning the sensor arm against the cam.

23. The spirometer of claim 16 wherein the curved passageway has a fixed radius of curvature and the vane is pivotally mounted in the passageway on an axis centrally offset from the radius of curvature.

24. A spirometer comprising:
a housing containing a curved passageway having a center of curvature;
a vane pivotally mounted within the housing at a location offset from the center of curvature of the curved passageway;
biasing means for biasing the vane to a first position against an inner end of a bore extending into the housing, the vane positioned substantially perpendicular to the bore when in the first position; and
measuring means for measuring over time the position of the vane within the housing.

25. The spirometer of claim 24 wherein the means for measuring comprises a cam movable with said vane, a sensor are engaged against said cam, a magnet on the sensor arm, and a Hall Effect device adjacent to the sensor arm.

26. The spirometer of claim 24 further comprising processing means linked to the measuring means for determining a diagnostic parameter from the position of the vane measured over time.

27. The spirometer of claim 26 further comprising reporting means linked to the processing means for reporting a diagnostic parameter to the user.

28. The spirometer of claim 26 wherein the processing means includes a microprocessor and a clock for computing the position of the vane, as a function of time, and producing a corresponding analog output; and
an analog-to-digital converter and a memory linked to the microprocessor for producing a digital diagnostic parameter from the analog output.

29. The spirometer of claim 24 further comprising tensioning means for tensioning movement of the vane.

30. The spirometer of claim 24 further comprising a plurality of closely spaced apertures extending from the curved passageway through the housing.

31. The spirometer of claim 24 further comprising a door positioned adjacent to the bore for closing off the bore when the spirometer is not in use.

32. A spirometer comprising:
a housing containing a curved passageway having a center of curvature;
a vane pivotally mounted within the housing at a location offset from the center of curvature of the curved passageway;
biasing means for biasing the vane to a first position against an inner end of a bore extending into the housing, the vane positioned substantially perpendicular to the bore when in the first position;
a cam moveable with said vane;
a sensor engaged against said cam;
a Hall effect device and a magnet associated with the sensor arm for measuring positions of the sensor arm and corresponding positions of said vane;
processing means linked to said Hall effect device, for converting positions of the sensor arm, as measured by the Hall effect device, to a diagnostic parameter; and
reporting means linked to said processing means for reporting the diagnostic parameter.

* * * * *